United States Patent
Wu et al.

(10) Patent No.: US 6,642,385 B2
(45) Date of Patent: Nov. 4, 2003

(54) SYNTHESIS OF 4-(PIPERIDYL)(2-PYRIDYL) METHANONE-(E)-O-METHYLOXIME AND SALTS

(75) Inventors: Wenxue Wu, Princeton Jct, NJ (US); Hongbiao Liao, Edison, NJ (US); David J Tsai, Warren, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/269,786

(22) Filed: Oct. 11, 2002

(65) Prior Publication Data

US 2003/0105136 A1 Jun. 5, 2003

Related U.S. Application Data

(60) Provisional application No. 60/329,561, filed on Oct. 15, 2001, and provisional application No. 60/329,562, filed on Oct. 15, 2001.

(51) Int. Cl.[7] ............................................. C07D 401/06
(52) U.S. Cl. ....................................... 546/193; 546/194
(58) Field of Search ................................. 546/193, 194

(56) References Cited

PUBLICATIONS

Niemers et al, "Pyridylalkyl–substituted amines" CA 86: 106314 (1977).*

Palani, A. et al.: "Discovery of 4–[(Z)–(4– Bromophenyl)–(ethoxyimino)methyl]–1'–[(2,4–dimethyl– 3–pyridinyl)carbonyl]–4'–methyl–1– 4'bipiperidine N–Oxide (SCH 351125): An Orally Bioavailable Human CCR5 Antagonists for the Treatment of HIV Infection" *J. Med. Chem*, 44(21), 3339–3342 (2001).

Piwinski, J. et al.: "Dual Antagonists of Platelet Activating Factor and Histamine. Identification of Structural Requirements for Dual Activity of N–Acyl–4–(5,6–dihydro–11 H–benzo[5,6]cyclohepta–[1,2–b] pyridin–11–ylidene)piperidines" *J. Med. Chem.* 34(1), 457–461 (1991).

* cited by examiner

*Primary Examiner*—Patricia L. Morris
(74) *Attorney, Agent, or Firm*—Palaiyur S. Kalyanaraman

(57) ABSTRACT

In one embodiment, the present invention describes the synthesis of 4-(piperidyl)(2-pyridyl)methanone-(E)-O-methyloxime dihydrochloride, monohydrochloride and free base, and similar compounds, in high stereochemical purity.

20 Claims, No Drawings

SYNTHESIS OF 4-(PIPERIDYL)(2-PYRIDYL) METHANONE-(E)-O-METHYLOXIME AND SALTS

FIELD OF THE INVENTION

This application specifically discloses a novel process to synthesize 4-(piperidyl) (2-pyridyl)methanone-(E)-O-methyloxime and its salts in high stereochemical purity. It also generically discloses a process to prepare compounds similar to the above in high stereochemical purity. This application claims priority from U.S. provisional application, Serial No. 60/329,561 filed on Oct. 15, 2001. The invention disclosed herein is related to that disclosed in the provisional patent application, Serial No. 60/329,562 filed on Oct. 15, 2001.

BACKGROUND OF THE INVENTION 4-(Piperidyl) (2-pyridyl)methanone-(E)-O-methyloxime dihydrochloride (Formula I) is an intermediate used in the preparation of compounds that are histamine-$H_3$ antagonists. An example of such histamine-$H_3$ antagonists is 1-[[1-[(2-Amino-5-pyrimidinyl)methyl]-4-piperidinyl]carbonyl]-4-[(E)-(methoxyimino)-2-pyridinylmethyl]piperidine shown in Formula II.

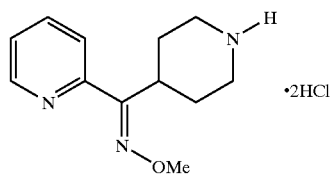

I

·2HCl

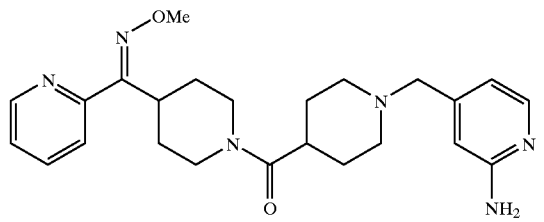

II

The conversion of the compound of Formula I into a compound of Formula II is disclosed in the commonly owned U.S. patent application, Ser. No. 09/978,267 (Attorney Docket No. AL01348K) filed of even date herewith. Antagonists of the $H_3$ receptor are useful for the treatment of allergy, asthma and other such respiratory disorders.

In view of the importance of the antagonists of histamine-$H_3$, new, novel methods of making such antagonists and/or their intermediates are always of interest.

SUMMARY OF THE INVENTION

In an embodiment, the present application teaches a novel, simple process of making a compound of Formula I, its monohydrochloride and its free base itself in high stereochemical purity and, via that process, a method of making a compound of Formula II in high yields and high stereochemical purity. The term "high stereochemical purity" refers to at least about 90% of the desired isomer, which, in the present invention, is the E-isomer of the compound of Formula I, its monohydrochloride and its free base. Indeed, the stereochemical purity of the compound of Formula I, its monohydrochloride and its free base made by the inventive process typically exceeds 95% of the E-isomer. The term "high yields" refers to at least about 60% yield of the desired product.

Thus, the present process comprises synthesizing compounds such as the compound of Formula I, its mono acid salt (for example, its monohydrochloride) and its free base from a compound of Formula III:

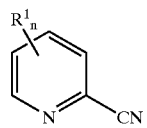

III where $R^1$ is defined below and n is a number from 1 to 4, and from a compound of Formula IV:

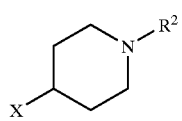

IV where $R^2$ is defined below. The process of making a compound such as the compound of Formula I from a compound of Formula III and a compound of Formula IV comprises:

(a) converting the compound of Formula IV into its Grignard form of Formula IVA:

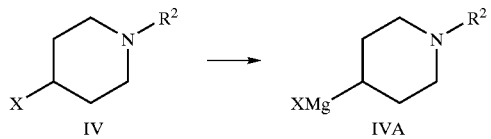

where $R^2$ is defined below and X is a halogen;

(b) reacting the compound of Formula III with the compound of Formula IVA to obtain a compound of Formula V:

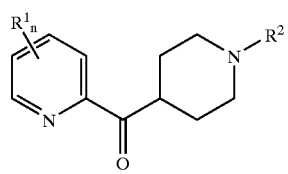

V (c) reacting the compound of Formula V with a suitable alkyl chloroformate of Formula VI:

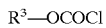

$R^3$—OCOCl

VI where $R^3$ is defined below, to yield a compound of Formula VII:

VII

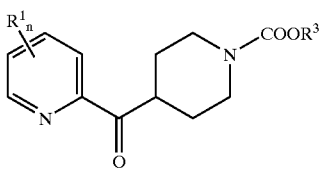

(d) forming the free base (Formula VIIA) and then the acid salt (mono acid salt or diacid salt) of the free base (Formula VIII):

VIIA

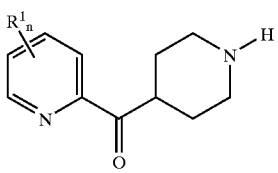

VIII

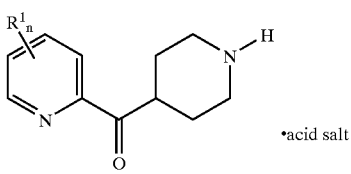

•acid salt (e) reacting the compound of Formula VIII with an alkoxyamine ($NH_2OR^4$) or its hydrochloride (where $R^4$ is defined below) to form an oxime of Formula IX:

IX

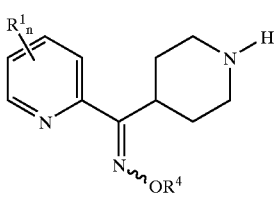

and (f) isomerizing the compound of Formula IX predominantly to the E isomer by treatment with a strong acid and simultaneously converting to the desired acid salt of a compound such as the compound of Formula I with an enriched E isomer, wherein the E isomer predominates over the Z-isomer by at least a 90:10 ratio. The acid salt, which may be the mono acid salt or the diacid salt, may be optionally converted back to its free base, if so desired.

$R^1$, $R^2$, $R^3$ and $R^4$ may be the same or different and are independently selected from the group consisting of H, halogen, alkyl, aryl, alkoxy, aryloxy, aralkyl (with the alkyl being the linker), alkylaryl (with the aryl being the linker), heteroalkyl, heteroaryl, alkyl-heteroaryl, heteroaralkyl, cycloalkyl and cycloalkylalkyl, wherein said alkyl, aryl, alkoxy, aryloxy, arylalkyl, alkylaryl, heteroalkyl, heteroaryl, alkyl-heteroaryl, heteroaralkyl, cycloalkyl and cycloalkylalkyl may optionally be substituted with one or more chemically-suitable substituents independently selected from the group consisting of alkyl, alkenyl, alkynyl, aryl, aralkyl, cycloalkyl, heterocyclic and halogen. $R^1$ itself may be F, Cl, Br or I. The term "halogen" refers to F, Cl, Br or I. The acid-catalyzed isomerization in step (f) above is believed to be novel and offers the desired salt of the desired compound with the enriched E-isomer as noted above. When $R^1$ is H, n=1, $R^4$=methyl, and the acid used in step (f) for isomerization is HCl in the above sequence, the final product is the compound of Formula I.

The inventive process to make the compound of Formulas IX and I has several advantages: it is economical, can be easily scaled-up and yields the desired E-isomer in high yields and in high stereochemical purity.

DESCRIPTION OF THE INVENTION

In one embodiment, the present invention discloses a novel, easy-to-use process for preparing the compound such as the compound of Formula I in high yields and high stereochemical purity. Additionally, it teaches novel processes to prepare intermediates such as the compounds of Formulas V, VII, VIII and IX in high yields. The inventive process to prepare such compounds is schematically described below in Scheme 1:

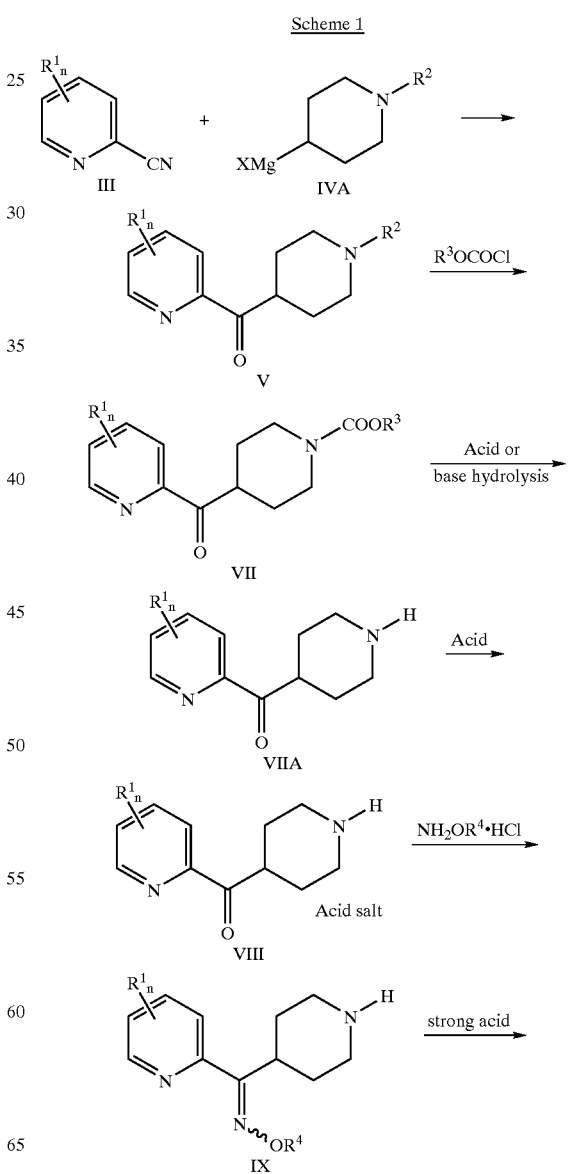

-continued

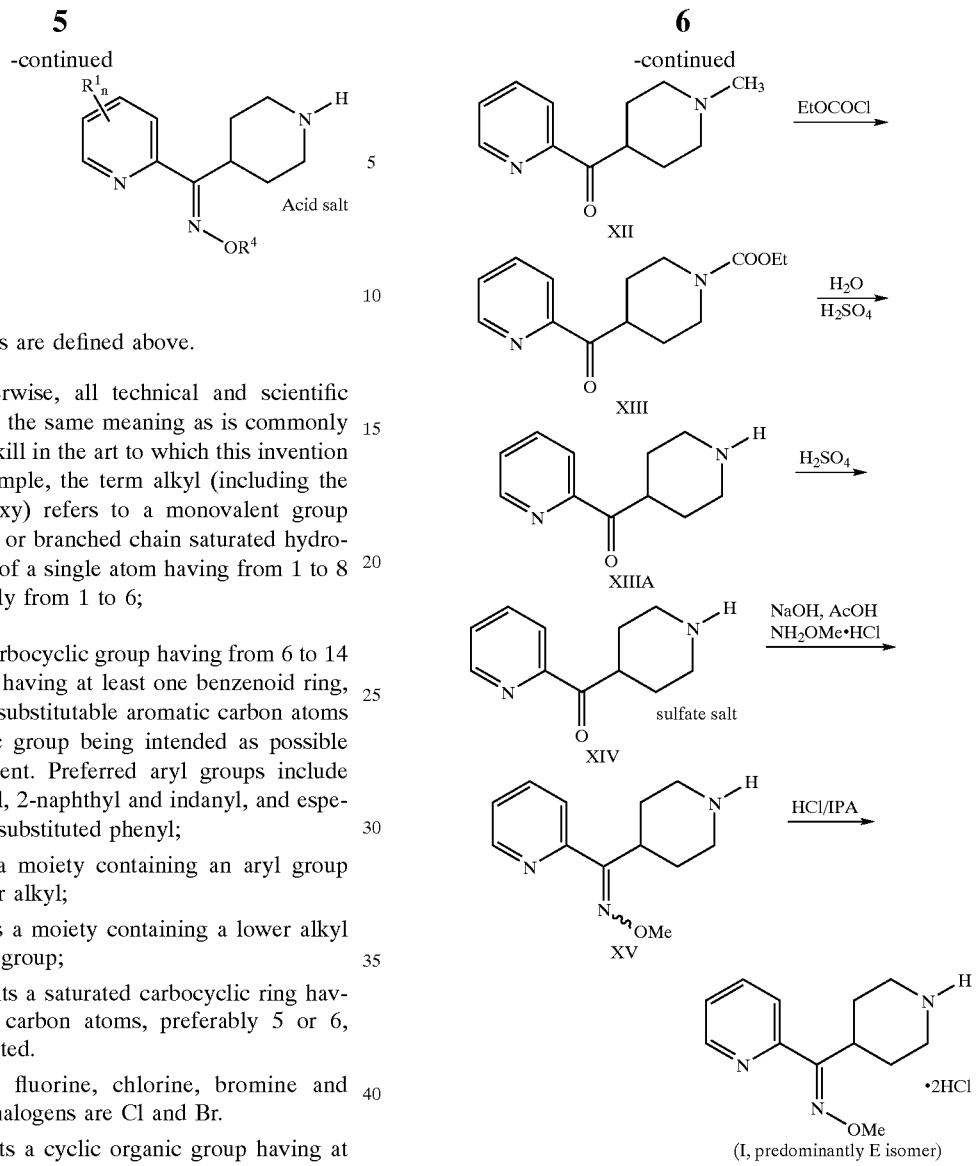

(I, predominantly E isomer)

where the various terms are defined above.

Unless defined otherwise, all technical and scientific terms used herein have the same meaning as is commonly understood by one of skill in the art to which this invention belongs. Thus, for example, the term alkyl (including the alkyl portions of alkoxy) refers to a monovalent group derived from a straight or branched chain saturated hydrocarbon by the removal of a single atom having from 1 to 8 carbon atoms, preferably from 1 to 6;

- aryl—represents a carbocyclic group having from 6 to 14 carbon atoms and having at least one benzenoid ring, with all available substitutable aromatic carbon atoms of the carbocyclic group being intended as possible points of attachment. Preferred aryl groups include phenyl, 1-naphthyl, 2-naphthyl and indanyl, and especially phenyl and substituted phenyl;
- aralkyl—represents a moiety containing an aryl group linked vial a lower alkyl;
- alkylaryl—represents a moiety containing a lower alkyl linked via an aryl group;
- cycloalkyl—represents a saturated carbocyclic ring having from 3 to 8 carbon atoms, preferably 5 or 6, optionally substituted.
- halogen—represents fluorine, chlorine, bromine and iodine; preferred halogens are Cl and Br.
- heteroaryl—represents a cyclic organic group having at least one O, S and/or N atom interrupting a carbocyclic ring structure and having a sufficient number of delocalized pi electrons to provide aromatic character, with the aromatic heterocyclic group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 4-imidazolyl, 2-, 4- or 5-pyrimidinyl, 2-pyrazinyl, or 3- or 4-pyridazinyl, etc. Preferred heteroaryl groups are 2-, 3- and 4-pyridyl; Such heteroaryl groups may also be optionally substituted.
- heteroalkyl—represents an alkyl group containing one or more heteroatoms.

The synthesis of the specific compound of Formula I, following the above-noted process, is exemplified in Scheme 2:

Scheme 2

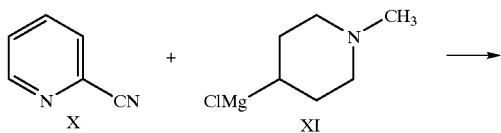

The compounds of the Formulas XII, XIII, XIIIA, XIV and XV and their isomers (where applicable) are believed to be novel compounds. As stated above, the inventive novel conversion of the compound of Formula XV to I surprisingly yields predominantly the E-isomer of the compound of Formula I in high stereochemical purity and high yields. Isomerization of a mixture of phenyl compounds by acid catalysis is discussed by T. Zsuzsanna et al, Hung.Magy.Km.Foly., 74(3) (1968), 116–119. While the preferred reagents and reaction conditions for the various steps in the inventive process are described in detail in the Examples section, the following summarizes the details for the generic synthesis according to Scheme 1.

The presently disclosed process starts with the compound of Formula IV. In step 1, a 4-halo-1-$R^2$ substituted piperidine is converted to its Grignard analog (IV) by reacting with magnesium. The reaction is performed generally at temperatures of about −10° C. to reflux. Generally a hydrocarbon solvent such as, for example, toluene, xylene, chlorobenzene, and the like, an ether such as, for example, a $C_5$–$C_{12}$ alkyl ether, 1,2-dimethoxyethane, 1,2-diethoxyethane, diglyme, 1,4-dioxane, tetrahydrofuran, methyl tetrahydrofuran, and the like, or a mixture of such solvents, is suitable for this reaction. The solution is cooled to around −10° C. to about 10° C. and then reacted with a suitable 2-cyanopyridine (III), for about 10–120 minutes. Examples of suitable 2-cyanopyridine are 2-cyanopyridine, 4-methyl-2-cyanopyridine, 4-ethyl-2-cyanopyridine, 4-phenyl-2-cyanopyridine, and the like. Preferred are 2-cyanopyridine and 4-methyl-2-cyanopyridine. Compounds such as, for example, Red-Al® (from Aldrich Chemical Company, Milwaukee, Wis.), iodine and the like, may be used as initiators in this reaction. The Grignard compound is used generally in about 1–4 molar equivalents with respect to the compound of formula III, preferably in about 1–3 molar equivalents and typically in about 1.5–2.5 molar equivalents. The product of formula V may be isolated by customary work-up procedures, such as, for example, treatment with an acid (e.g. HCl) preferably in a suitable solvent (e.g., tetrahydrofuran or ethyl acetate).

The product of Formula V may then be reacted with an alkyl chloroformate in the next step. Suitable alkyl chloroformates are, for example, methyl chloroformate, ethyl chloroformate, propyl chloroformate, benzyl chloroformate., and the like, with the preferred being methyl chloroformate or ethyl chloroformate. Generally a solvent such as, for example, toluene, xylene, chlorobenzene, methylene chloride, ethylene chloride, ethyl acetate, isobutyl acetate, n-butyl acetate, a $C_5$–$C_{12}$ alkyl ether, 1,2-dimethoxyethane, 1,2-diethoxyethane, diglyme, 1,4-dioxane, tetrahydrofuran, methyl tetrahydrofuran and the like is suitable for this reaction. The reaction is generally performed at about 25–100° C., preferably about 40–90° C. and typically about 50–80° C., for about 1–5 hours. After the reaction, generally the generated acid is washed off and the product of formula VII may be isolated by organic solvent extraction.

The compound of Formula VII may then be hydrolyzed to its free base (Formula VIIA) by acid (or base) hydrolysis, which may then be converted into its acid salt (Formula VIII) by treatment with an acid such as, for example, sulfuric acid, hydrochloric acid, trifluoroacetic acid and the like, generally in a solvent at temperatures between ambient and reflux of the solvent. Suitable solvent is water containing the acid whose salt is desired. The salt may be recrystallized. Suitable recrystallization solvents include water, water-miscible solvents such as, for example, acetonitrile, THF, ethanol, methanol, acetone and the like, and mixtures thereof; acetonitrile or acetonitrile-water mixture is preferred. There being two nitrogen atoms in the compound of Formula VIIA, the salt VIII may have 1 or 2 moles of acid.

The compound of Formula VIII may then be converted to an alkyloxime of Formula IX by reacting it with an alkoxyamine (or its hydrochloride), usually in a protic solvent; water is preferred. Suitable alkoxyamines are, for example, methoxyamine, ethoxyamine and the like. Methoxyamine is preferred. The alkoxyamine (or its hydrochloride) is employed generally in about 1 to about 4 molar equivalents, preferably in about 1 to about 3 molar equivalents, and typically in about 1 to about 2 molar equivalents, with respect to the compound of Formula VIII. Generally, the reaction is catalyzed by a weak acid such as, for example, acetic acid, formic acid and the like, or mixtures thereof. The pH may be adjusted to be about 3–6 if so desired. A cosolvent such as, for example, methanol, ethanol, isopropanol, n-butanol and the like, or mixtures thereof may be added, if so desired. The product of Formula IX, after work-up, is a mixture of the Z- and the E-isomers, whose ratio may be analyzed for its stereochemical make-up, using techniques well known in the art such as, for example, HPLC.

Since the desired isomer is the E-isomer, it would be advantageous to enrich the compound of Formula IX in the desired E-isomer. Applicants found that treating the compound of Formula IX with a strong acid under certain reaction conditions surprisingly isomerizes the mixture of the Z and the E-isomers into predominantly the E-isomer. Generally, the compound of Formula IX may be dissolved in a solvent such as, for example, ethanol, methanol, isopropanol, n-butanol and the like, ether such as methyl tert-butyl ether, tetrahydrofuran and the like, hydrocarbon such as, for example, heptane, hexane, toluene and the like, nitrile such as, for example, acetonitrile and the like, or mixtures of such solvents. It is then treated with a strong acid such as, for example, HCl, HBr, $H_2SO_4$ and the like, at temperatures in the range 20 to 100° C. for about 1–20 hours. The acid is employed generally in about 1 to about 10 molar equivalents, preferably in about 1 to about 8 molar equivalents, and typically in about 1 to about 6 molar equivalents. Work-up typically forms predominantly the acid salt of the E-isomer of the compound of Formula IX. Depending upon the reaction conditions, there may be one (e.g. 1HCl), or two (e.g. 2HCl) molar equivalents of the acid in the isolated E isomer, since the compound contains two nitrogen atoms. As one skilled in the art knows, the final product may optionally be converted to its free base with the E isomer still predominating, by reacting with standard processes such as, for example, treatment with a suitable base.

When $R^2=R^3=R^4$=methyl, n=1 and $R^1$=H, and the acid salt is 2HCl in the isolated E isomer compound, it is in fact the compound of Formula I. HPLC analysis (when $R^2=R^3=R^4$=methyl, n=1 and $R^1$=H and the acid salt is 2HCl) after a typical reaction sequence as shown in the Examples section showed the presence of the E-isomer generally in about 90% or above stereochemical purity, and typically in about 95% or above stereochemical purity in the isolated product. Additionally, the yields of the desired compound in such stereochemical purity was quite high, demonstrating that such isomerization reaction using a strong acid may be applicable to prepare E-isomers of such oximes in high yields and high stereochemical purity.

The products of the various steps in the reaction schemes described herein may be isolated and purified by conventional techniques such as, for example, filtration, recrystallization, solvent extraction, distillation, precipitation, sublimation, column chromatography and the like, as is well known to those skilled in the art. The products may be analyzed and/or checked for purity by conventional methods such as, for example, thin layer chromatography, NMR, HPLC, melting point, mass spectral analysis, elemental analysis and the like, well known to those skilled in the art.

The following nonlimiting EXAMPLES are provided in order to further illustrate the present invention. While the EXAMPLES are described herein as the preparation of the compound of Formula I from the compound of Formula X as shown in Scheme 2, it will be apparent to those skilled in the art that many modifications, variations and alterations to the present disclosure, both to materials, methods and reaction conditions, may be practiced. All such modifications, variations and alterations are intended to be within the spirit and scope of the present invention.

EXAMPLES

Unless otherwise stated, the following abbreviations have the stated meanings in the Examples below:

HPLC=High Performance Liquid Chromatography

M.pt: melting point

NMR=nuclear magnetic resonance spectroscopy

DMSO=dimethylsulfoxide
mL=milliliters
g=grams
rt=room temperature (ambient)

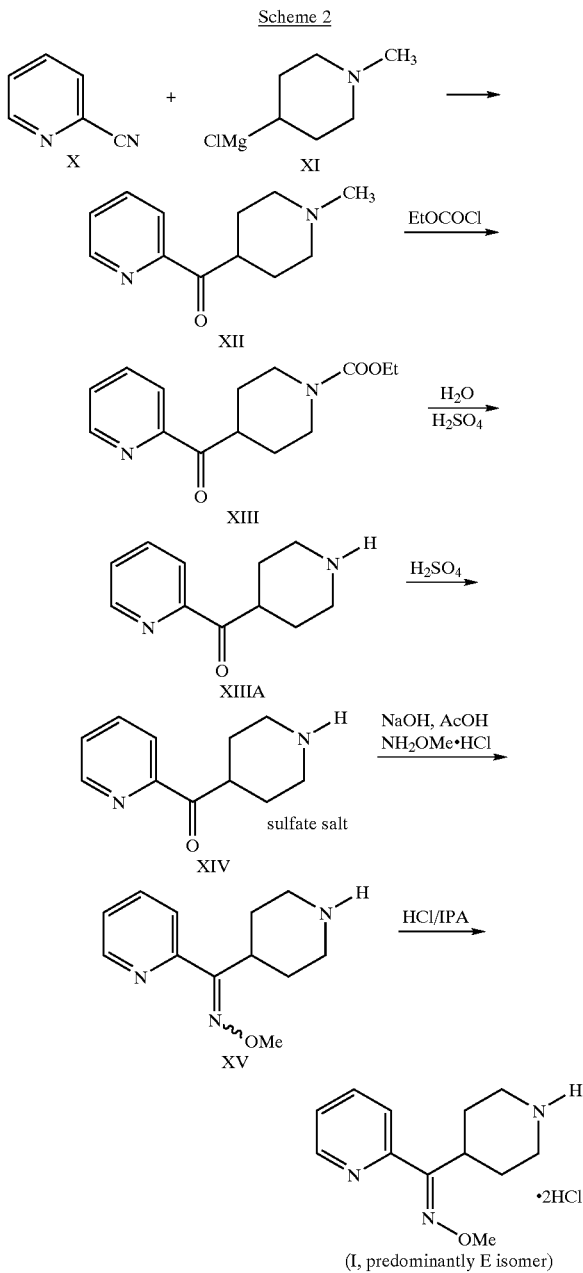

Example 1

Preparation of the Compound of Formula XII

To a suspension of magnesium chips (110 g) in THF (2800 mL) was added Red-Al® (9 mL, 65% solution of sodium bis(2-methoxyethoxy)aluminum hydride in toluene). The mixture was heated at reflux for 1 h and then cooled to room temperature. 4-chloro-1-methylpiperidine (71 mL) was added and the mixture was heated at gentle reflux for 30 min or until the Grignard reaction was initiated. The main portion of 4-chloro-1-methylpiperidine (633 mL) was then added over 60 min while maintaining the reaction mixture at gentle reflux. After the addition was complete, the mixture was heated at reflux for 5 h and then cooled to −5 to 0° C. A solution of 2-cyanopyridine (281 g, from Aldrich Chemical Company) in THF (560 mL) was added over 1 h at −5 to 5° C. The mixture was stirred at −5 to 5° C. for 30 min and poured into a mixture of concentrated hydrochloric acid (600 mL) and ice (3000 g). The phases were separated. To the aqueous layer was added sodium chloride (600 g) and the resulting solution was extracted with THF (2200 mL) three times. The organic layers were combined and concentrated under vacuum to give a brown oil (501 g). The oil was found to be 86.1% pure by HPLC analysis against a pure standard. The crude material could be used directly in the next step or purified, if so desired. The crude product was purified by vacuum distillation to give a yellow oil which solidified upon cooling (b.p.: 120–125° C./0.5 torr, low melting solid). $^1$H NMR (400 MHz, CDCl$_3$): δ 8.42 (dd, $J_1$=3.3 Hz, $J_2$=0.9 Hz 1H), 7.76 (d, J=7.8 Hz, 1H), 7.58 (dt, $J_1$=7.7 Hz, $J_2$=1.7 Hz, $J_2$=1.7 Hz, 1H), 7.21 (ddd, $J_1$=7.5 Hz, $J_2$=4.8 Hz, $J_3$=1.2 Hz, 1H), 3.56 (tt, $J_1$=11.5 Hz, $J_2$=3.8 Hz, 1H), 2.65 (m, 2H), 2.03 (s, 3H), 1.85 (dt, $J_1$=11.7 Hz, $J_2$=2.5 Hz, 2H), 1.67 (br d, J=12.4 Hz, 2H), 1.53 (m, 2H).

Example 2

Preparation of the Compound of Formula XIII

A sample of crude compound of Formula XII (from Example 1) (249 g, 60.4% purity) was azeotropically dried in toluene. To the dried solution in toluene (2000 mL) was added ethyl chloroformate (169 mL) over 30 min at 70–75° C. The reaction mixture was heated at 70–80° C. for 2 h and cooled to room temperature. An aqueous potassium bicarbonate solution (300 ml, 25%) was added over 30 min at 20 to 30° C. After stirring at room temperature for 15 min, the mixture was settled and the phases were separated. The organic layer was washed with 10% aqueous acetic acid (1000 mL) followed by water (1000 mL). The organic layer thus obtained (2720 mL) was found to contain 170 g of the compound of Formula XIII by HPLC analysis against a pure standard. The toluene solution can be used directly for the preparation of the compound of Formula XIV.

An analytically pure sample of the compound of Formula XIII was obtained by flash column chromatography (pale yellow solid, m.p. 54.4° C.). $^1$H NMR (400 MHz, CDCl$_3$): δ 8.70 (dd, $J_1$=5.3 Hz, $J_2$=0.9 Hz, 1H), 8.05 (d, J=7.8 Hz, 1H), 7.86 (dt, $J_1$=7.7 Hz, $J_2$=1.7 Hz, 1H), 7.50 (m, 1H), 4.23 (brs, 2H), 4.15 (q, J=7.1 Hz, 2H), 4.05 (tt, $J_1$=11.5 Hz, $J_2$=3.9 Hz, 1H), 2.99 (brt, J=11.6, 2H), 1.91 (brs, 2H), 1.65 (dq, $J_1$=2.2 Hz, $J_2$=3.6 Hz, 2H), 1.28 (t, J=7.1 Hz, 3H).

Example 3

Preparation of the Compound of Formula XIIIA and Conversion Into the Compound of Formula XIV The above toluene solution (from Example 2) was extracted into 50% v/v sulfuric acid (330 mL) and the acid layer was heated at 90–100° C. for 20 h. The mixture was cooled to 50–60° C. and diluted with acetonitrile (2000 mL) and seeded. The mixture was cooled to room temperature and was filtered. The wet product was washed with acetonitrile and dried at 55–65° C. under vacuum (248 g, brown solid).

Example 4

Preparation of the Compound of Formula XIV from the Compound of Formula XII A sample of crude compound of Formula XII (240 g, 86.1% purity) was azeotropically dried in toluene. To the dried solution in toluene (2000 mL) was added ethyl chloroformate (169 mL) over 30 min at 70–75° C. The reaction mixture was heated at 70–80° C. for 5 h, over which time, triethylamine (21 mL) and more ethyl chloroformate (22 mL) were added. An aqueous potassium bicarbonate solution (300 ml, 25%) was added over 30 min at 20 to 30° C. After stirring at room temperature for 15 min, the mixture was settled and the phases were separated. The organic layer was washed with 10% aqueous acetic acid (1000 mL) followed by water (1000 mL). The organic layer was extracted into 50% v/v sulfuric acid (450 mL) and the acid layer was heated at 90–100° C. for 16 h. The mixture was cooled to 50–60° C. and diluted with acetonitrile (2000 mL) and seeded. The mixture was cooled to room temperature and was filtered. The wet product was washed with acetonitrile and dried at 55–65° C. under vacuum (360 g, off-white solid, m.p.: 247° C. dec.). $^1$H NMR (400 MHz, DMSO-$d_6$): 10.68 (brs, 3H), 8.76 (m, 1H), 8.63 (brs, 1H), 8.33 (brs, 1H), 8.03 (m, 2H), 7.72 (ddd, $J_1$=7.4 Hz, $J_2$=4.8 Hz, $J_3$=1.4 Hz, 1H), 4.09 (tt, $J_1$=11.4 Hz, $J_2$=3.5 Hz, 1H), 3.34 (br d, J=12.6 Hz, 2H), 3.08 (br q, J=11.8 Hz, 2H), 2.02 (br d, J=12.6 Hz, 2H), 1.74 (m, 2H).

Example 5

Preparation of the Compound of Formula XV

To a solution of the compound of Formula XIV (150 g) in water (300 mL) was added 25% sodium hydroxide (270 mL) while maintaining temperature below 60° C. Acetic acid (34 mL) was added followed by 25–30% aqueous solution of methoxyamine hydrochloride (180 mL). The pH of the mixture was adjusted to be 3–6. The mixture was heated at 50–60° C. for about 3 h. After the mixture is cooled to room temperature, 25% sodium hydroxide was added (150 mL) and the mixture was extracted with toluene (376 mL) twice. The organic layers were combined and concentrated under vacuum to give the free base (mixture of E and Z isomers in about 53:47 ratio by HPLC analysis).

Example 6

Isomerization to I as Predominantly the E Isomer

After being azeotropically dried, the free base from Example 5 was dissolved in toluene (375 mL) and added to 5–6 N hydrochloric acid in isopropanol (300 mL). The mixture was heated at 60–70° C. for 3 h, during which time the product crystallized out. The mixture was cooled to room temperature, filtered, and washed with isopropanol (300 mL). It was dried at 50–60° C. to give an white solid (106.8 g, m.p.: 197° C. dec., E/Z ratio: 97:3 by HPLC analysis). $^1$H NMR (400 MHz, $D_2O$, E isomer): δ 8.61 (dd, $J_1$=6.1 Hz, $J_2$=1.2 Hz, 1H), 8.48 (dt, $J_1$=1.5 Hz, $J_2$=8.0 Hz, 1H), 8.12 (d, J=8.3 Hz, 1H), 7.90 (ddd, $J_1$=7.7 Hz, $J_2$=5.9 Hz, $J_3$=1.0 Hz 1H), 3.99 (s, 3H), 3.39 (m, 2H), 3.30 (tt, $J_1$=3.5 Hz, $J_2$=12.4 Hz, 1H), 2.94 (dt, $J_1$=2.6 Hz, $J_2$=13.2 Hz, 2H), 2.37 (dq, $J_1$=3.9 Hz, $J_2$=13.5 Hz, 2H), 1.93 (br d, J=14.2 Hz, 2H).

What is claimed is:

1. A process for preparing a compound of the Formula:

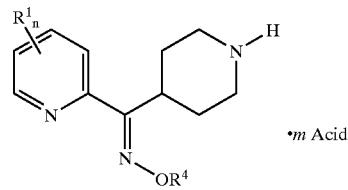

·m Acid where $R^1$ and $R^4$ are defined below, m is 1 or 2, and n is a number from 1 to 4, and wherein said compound is in its E-isomer form in at least about 90% stereochemical purity, from a compound of Formula III:

III and from a compound of Formula IV:

IV where $R^2$ is defined below and X is a halogen, said process comprising:

(a) converting the compound of Formula IV, where $R^2$ is defined below and X is a halogen, into its Grignard form of Formula IVA:

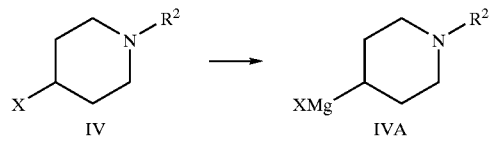

by reacting said compound of Formula IV with magnesium in a solvent selected from the group consisting of toluene, xylene, 1,2-dimethoxyethane, 1,2-diethoxyethane, diglyme, 1,4-dioxane, tetrahydrofuran, methyl tetrahydrofuran and mixtures thereof, at about –10° C. to reflux of said solvent;

(b) reacting the compound of Formula III with the compound of Formula IVA in the presence of an initiator at about –10 to 10° C. to obtain a compound of Formula V:

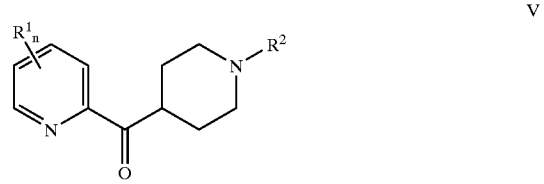

V (c) reacting the compound of Formula V with an alkyl chloroformate of Formula VI:

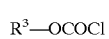

VI where $R^3$ is defined below, in a solvent selected from the group consisting of toluene, xylene, chlorobenzene, methylene chloride, ethylene chloride, ethyl acetate, isobutyl acetate, n-butyl acetate, 1,2-dimethoxyethane, 1,2-diethoxyethane, diglyme, 1,4-dioxane, tetrahydrofuran, methyl tetrahydrofuran and mixtures thereof, at about 25–100° C., for about 1–5 hours, to yield a compound of Formula VII:

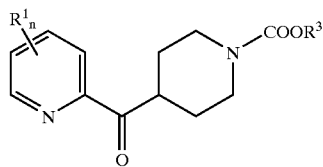

VII (d) hydrolyzing the compound of Formula VII into its free base of Formula VIIA, by acid hydrolysis or base hydrolysis:

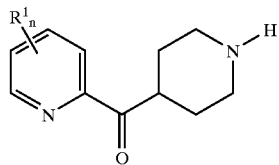

VIIA (e) Forming the acid salt (Formula VIII) from the compound of Formula VIIA by reacting with aqueous sulfuric acid, hydrochloric acid, or trifluoroacetic acid:

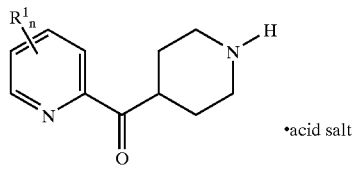

VIII wherein said acid salt refers to sulfate, hydrochloride or trifluoroacetate;

(f) reacting the acid salt of Formula VIII with an alkoxyamine ($NH_2OR^4$) or its hydrochloride in a protic solvent in the presence of a weak acid to form an oxime of Formula IX:

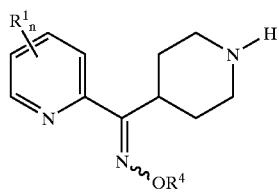

IX where $R^4$ is defined below, and (g) isomerizing the compound of Formula IX by treatment with a strong acid and simultaneously converting to the desired acid salt of Formula IX with an enriched E isomer, wherein the E isomer predominates over the Z-isomer by at least a 90:10 ratio, wherein $R^1$, $R^2$, $R^3$ and $R^4$ may be the same or different and are independently selected from the group consisting of H, halogen, alkyl, aryl, alkoxy, aryloxy, arylalkyl (with the alkyl being the linker), alkylaryl (with the aryl being the linker), heteroalkyl, heteroaryl, alkyl-heteroaryl, heteroaralkyl, cycloalkyl and cycloalkylalkyl, and wherein said alkyl, aryl, alkoxy, aryloxy, arylalkyl, alkylaryl, heteroalkyl, heteroaryl, alkyl-heteroaryl, heteroaralkyl, cycloalkyl and cycloalkylalkyl may optionally be substituted with one or more substituents independently selected from the group consisting of alkyl, alkenyl, alkynyl, aryl, aralkyl, cycloalkyl, heterocyclic and halogen.

2. The process of claim 1, wherein X is Cl or Br, m is 2, $(R^1)_n$ is H, and $R^2=R^3=R^4$=alkyl.

3. The process of claim 2, wherein X is Cl and $R^2=R^3=R^4$=methyl or ethyl.

4. The process of claim 1, wherein said solvent in step (a) is tetrahydrofuran.

5. The process of claim 1, wherein said initiator is sodium bis(2-methoxyethoxy)aluminum hydride or iodine.

6. The process of claim 1, wherein in step (b) said compound of Formula IVA is employed in about 1–4 molar ratio with respect to said compound of Formula III.

7. The process of claim 1, wherein in step (c), said alkyl chloroformate is selected from the group consisting of methyl chloroformate, ethyl chloroformate, propyl chloroformate and benzyl chloroformate.

8. The process of claim 7, wherein said alkyl chloroformate is ethyl chloroformate.

9. The process of claim 1 wherein said solvent in step (c) is toluene.

10. The process of claim 1, wherein said acid salt is sulfate.

11. The process of claim 10, wherein said sulfate VIII is recrystallized from a solvent selected from the group consisting of water, acetonitrile, THF, ethanol, methanol, acetone and the like and mixtures thereof.

12. The process of claim 11, wherein said solvent is acetonitrile-water mixture.

13. The process of claim 1, wherein said alkoxyamine in step (f) is methoxyamine or methoxyamine hydrochloride, and said acid is acetic acid.

14. The process of claim 13, wherein said methoxyamine or methoxyamine hydrochloride is present in about 1–4 molar equivalents, with respect to the compound of Formula VIII, and the pH of the reaction is about 3–6.

15. The process of claim 1, wherein said strong acid in step (g) is selected from the group consisting of HCl, HBr and $H_2SO_4$, and said treatment of the compound of Formula VI comprises reacting with said strong acid in a solvent at about 20 to 100° C. for about 1–20 hours.

16. The process of claim 15, wherein said acid is HCl.

17. The process of claim 16, wherein said HCl is present in about 1–10 molar equivalents, with respect to the compound of Formula IX.

18. The process of claim 17, wherein said HCl is present in about 1–8 molar equivalents.

19. The process of claim 15, wherein said solvent is selected from the group consisting of ethanol, methanol, isopropanol, n-butanol, methyl tert-butyl ether, tetrahydrofuran, heptane, hexane, toluene, acetonitrile, ethyl acetate and mixtures thereof.

20. The process of claim 19, wherein said solvent is a mixture of isopropyl alcohol and toluene.

* * * * *